United States Patent

Alnafisah

(10) Patent No.: US 8,825,229 B2
(45) Date of Patent: Sep. 2, 2014

(54) MOBILE TRACKING AND SUBDUING APPARATUS, METHOD, AND COMPUTER PROGRAM PRODUCT

(76) Inventor: Khalid Hamad Alnafisah, Ruston, LA (US)

( * ) Notice: Subject to any disclaimer, the term of this patent is extended or adjusted under 35 U.S.C. 154(b) by 57 days.

(21) Appl. No.: 13/545,063

(22) Filed: Jul. 10, 2012

(65) Prior Publication Data

US 2014/0018769 A1 Jan. 16, 2014

(51) Int. Cl.
*B64C 39/02* (2006.01)

(52) U.S. Cl.
USPC .............. 701/3; 701/23; 244/75.1; 244/3.11

(58) Field of Classification Search
CPC .......... B64C 39/024; B64F 1/02; B64F 1/04; B64F 5/00; B64F 1/06; B64F 1/12; B64F 5/0081; B64F 5/0009; B64F 5/0045; G06T 2207/30252; G06T 2207/10016; G06T 2207/10021; G06T 2207/10032; G06T 2207/30181; G06T 15/06; G06T 2200/32; G06T 2207/01
USPC ........ 701/1, 16, 24, 13, 120; 89/41.17, 41.05, 89/204, 1.8; 342/453, 385; 340/10.1; 244/7 A, 75.1, 73 R, 72, 49, 48, 38, 244/3.17, 22, 1 TD, 1 N, 17.25, 17.23, 244/137.1, 118.1, 10
See application file for complete search history.

(56) References Cited

U.S. PATENT DOCUMENTS

| | | | | |
|---|---|---|---|---|
| 6,082,671 A | * | 7/2000 | Michelson | 244/72 |
| 8,167,234 B1 | * | 5/2012 | Moore | 244/17.25 |
| 2007/0150106 A1 | * | 6/2007 | Hashimoto et al. | 700/245 |
| 2011/0009807 A1 | * | 1/2011 | Kjeken et al. | 604/21 |
| 2012/0248243 A1 | * | 10/2012 | Greenyer | 244/72 |
| 2012/0256730 A1 | * | 10/2012 | Scott et al. | 340/10.1 |
| 2013/0020428 A1 | * | 1/2013 | Miller et al. | 244/3.17 |

OTHER PUBLICATIONS

KR 2012072068 A_abstracted file.*

* cited by examiner

*Primary Examiner* — Helal A Algahaim
*Assistant Examiner* — Jelani Smith
(74) *Attorney, Agent, or Firm* — Oblon, Spivak, McClelland, Maier & Neustadt, L.L.P.

(57) ABSTRACT

A mobile tracking and subduing apparatus of a target object that includes liquid storage tank that is configured hold a predetermined amount of a liquid, a probe configured to inject the liquid from the liquid storage tank into a skin surface of a target object, an optical detection unit for obtaining image or video data, a GPS unit that generates positional data, a wireless communications interface configured to receive command data, and a target tracking unit for detecting and tracking the target object based on the received positional data, command data, and images or video data and inject the contents of the liquid storage section into the target object via the probe.

18 Claims, 8 Drawing Sheets

MOBILE TRACKING AND SUBDUING APPARATUS, METHOD, AND COMPUTER PROGRAM PRODUCT

BACKGROUND

GRANT OF NON-EXCLUSIVE RIGHT

This application was prepared with financial support from the Saudi Arabian Cultural Mission, and in consideration therefore the present inventor(s) has granted The Kingdom of Saudi Arabia a non-exclusive right to practice the present invention.

FIELD OF THE DISCLOSURE

Embodiments described herein relate generally to an apparatus, method, and computer program product for tracking and subduing a target object. More particularly, the embodiments described relate to an apparatus that can detect, identify, track, and subdue or incapacitate a target object.

SUMMARY

According to an embodiment, there is provided a mobile tracking and subduing apparatus of a target object that includes a liquid storage tank that is configured hold a predetermined amount of a liquid, a probe configured to inject the liquid from the liquid storage tank into a skin surface of a target object, an optical detection unit for obtaining image or video data, a GPS unit that generates positional data, an antenna configured to transmit and receive communication data, and a target tracking processor for detecting and tracking the target object based on the received positional data, communication data, and images or video data, and inject the contents of the liquid storage section into the target object via the probe while the target object is being tracked.

According to another embodiment, there is also provided a method of a mobile tracking and subduing apparatus comprising receiving communication data, generating positional data, detecting a target object through image or video data, tracking the detected target object based on the communication data, positional data, and image or video data and injecting a liquid into the target object based on the tracking.

According to another embodiment, there is provided a mobile tracking and subduing apparatus of a target object developed and fabricated using nanotechnology and nanostructures.

The foregoing paragraphs have been provided by way of general introduction, and are not intended to limit the scope of the following claims. The described embodiments, together with further advantages, will be best understood by reference to the following detailed description taken in conjunction with the accompanying drawings.

BRIEF DESCRIPTION OF THE DRAWINGS

A more complete appreciation of the present advancements and many of the attendant advantages thereof will be readily obtained as the same becomes better understood by reference to the following detailed description when considered in connection with the accompanying drawings. However, the accompanying drawings and the exemplary depictions do not in any way limit the scope of the advancements embraced by the specification. The scope of the advancements embraced by the specification and drawings are defined by the words of the accompanying claims.

DETAILED DESCRIPTION OF THE EMBODIMENTS

Figure 1:
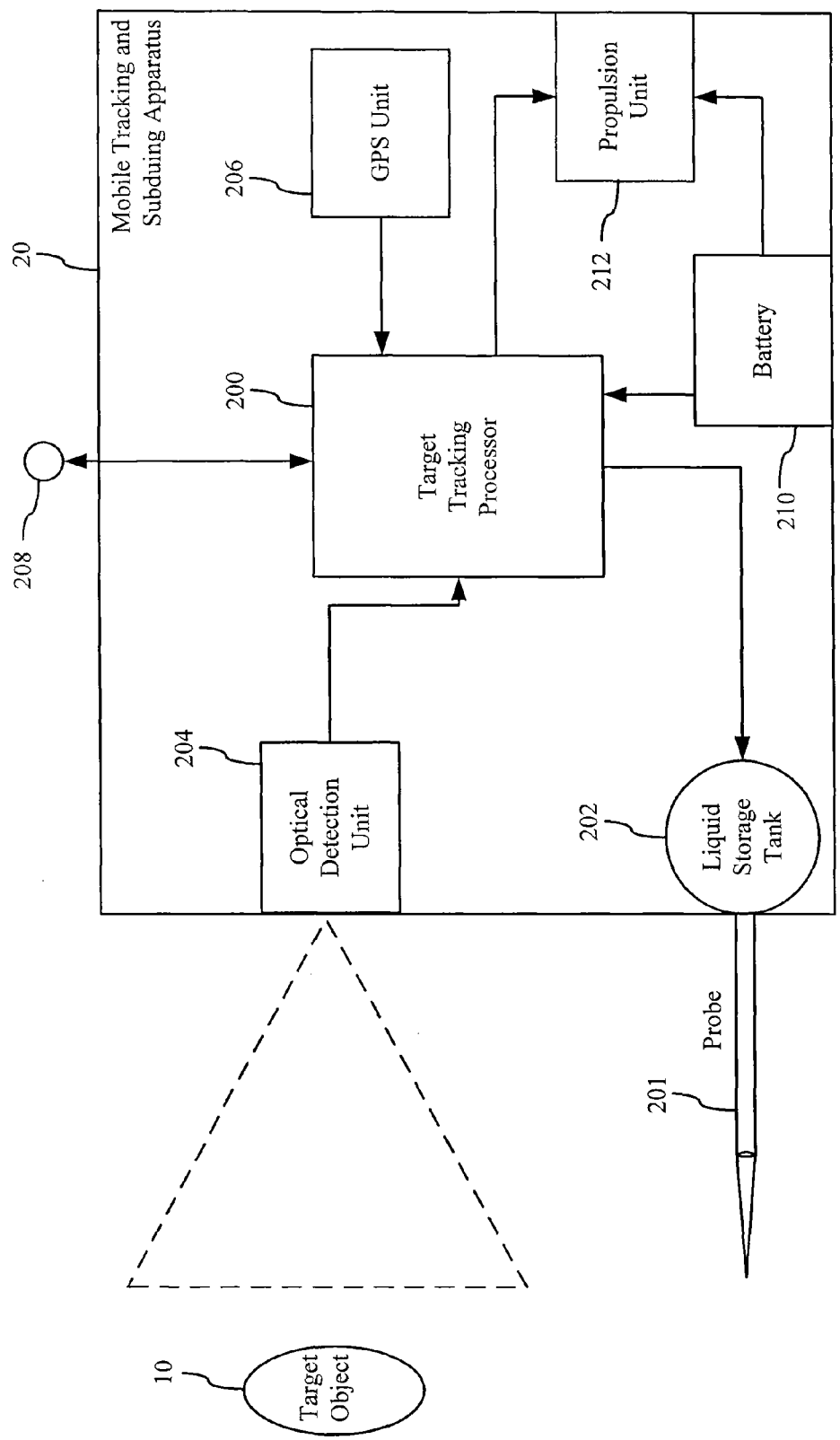
FIG. 1 is a block diagram of a mobile tracking and subduing apparatus according to an exemplary embodiment.

The mobile tracking and subduing apparatus described in the following paragraphs is designed, for example, to be part of a micro aerial vehicle (MAV) platform. MAV's are smaller versions of typical unmanned aerial vehicles (UAV) and have a wide array of uses driven by commercial, research, governmental, and military purposes. MAV's can even take the form of and perform similar behaviors of large insects or small birds similar to that of the MAV laid out in U.S. Pat. No. 8,167,234, which is herein incorporated by reference in its entirety.

MAV's are also better suited to provide a more inconspicuous platform for surveillance, incursion, and offensive payload deployment into area were danger exists to personnel. A MAV is an ideal platform to implement the mobile tracking and subduing apparatus when a target object to be detected, identified, and tracked is behind enemy lines or in an area when typical human surveillance and interaction would pose great risk to counter detection.

In addition the aerial platform, the mobile tracking and subduing apparatus is also suited to perform identification and tracking functionality as part of a micro land vehicle or a submerged platform. While the external environments and configurations of airborne, land born, and seaborne platforms vary substantially, the mobile tracking and subduing apparatus can perform similar functionality with respect to detection, identification, and tracking for each particular platform. In the following description, a mobile tracking and subduing apparatus as implemented on a MAV will be presented. It is relevant to note, however, that the mobile tracking and subduing apparatus can be implemented on any appropriate vehicle or platform in any environment.

Referring now to the drawings, wherein like reference numerals designate identical or corresponding parts throughout several views.

FIG. 1 is a block diagram of a mobile tracking and subduing apparatus 20 for tracking and subduing a target object 10 according to an exemplary embodiment. The mobile tracking and subduing apparatus 20 includes a target tracking processor 200, a probe 201, a liquid storage tank 202, an optical detection unit 204, a GPS unit 206, an antenna 208, a battery 210, and a propulsion unit 212.

The target object 10 can be any type of object or organism such as a human or an animal that is to be the subject of detection, identification, tracking, and subduing. The target object can be a particular or distinct human or animal as well as one of a plurality of common targets. For example, the target object may be respective humans within an unruly crowd or a particular human within the crowd.

The target tracking processor 200 receives communication data from a remote facility, such as a command center, and transmits over a predetermined frequency plan over a wireless network such as a cellular network, WiFi network, satellite network, a combination of these, and the like. Communication data may include potential location data of the target object 10, potential identification data of the target object 10, or any other information related to locating and identifying the target object 10. The communication data may also include flight control information that controls the flight operations of the MAV platform in which the mobile tracking and subduing apparatus 20 has been implemented. Once a determination has been made that the target object has been detected, the target tracking processor 200 will provide flight commands to the propulsion unit 212 to approach the target object and when close enough to the target object 10, transmit a control signal to the liquid storage tank 202 to inject a liquid into the target object 10 via the probe 201.

The liquid storing tank 202 is flexible so as to provide a positive or negative pressure liquid pulled/pushed from the probe 201. The liquid storing tank 202 also holds any type of liquid contents that has been developed to subdue or incapacitate the target object 10. The liquid contents are injected into the target object 10 via the probe 201. The probe 201 can be any form of injection device, such as a syringe or a needle, and can be configured to continuously be exposed or be retracted into a sheath to avoid damage to the point of the injection device. The probe illustrated in FIG. 1 is configured to be continuously exposed. Retracted probes can be extended from a sheath to inject the target object 10 via a spring mechanism, electronic device, or the such.

The optical detection unit 204 can be any image generating or sensing device as well as motion capture device. The images can be in color, black and white, infrared, or any other appropriate medium that can be processed by the target tracking processor 200. The optical detection unit 204 can also detect heat signatures from the target object. The GPS unit 206 received a GPS signal from a plurality of GPS satellites and calculates positional data that is used by the target tracking processor 200 in the identification and tracking functions.

The battery 210 supplies power to the mobile tracking and subduing apparatus 20. The battery 207 can be any form of power generation device that generates electrical power using a fuel source such as chemical, combustion, solar, wind, thermal, nuclear, biomass, electromagnetic, and the such.

Figure 2:
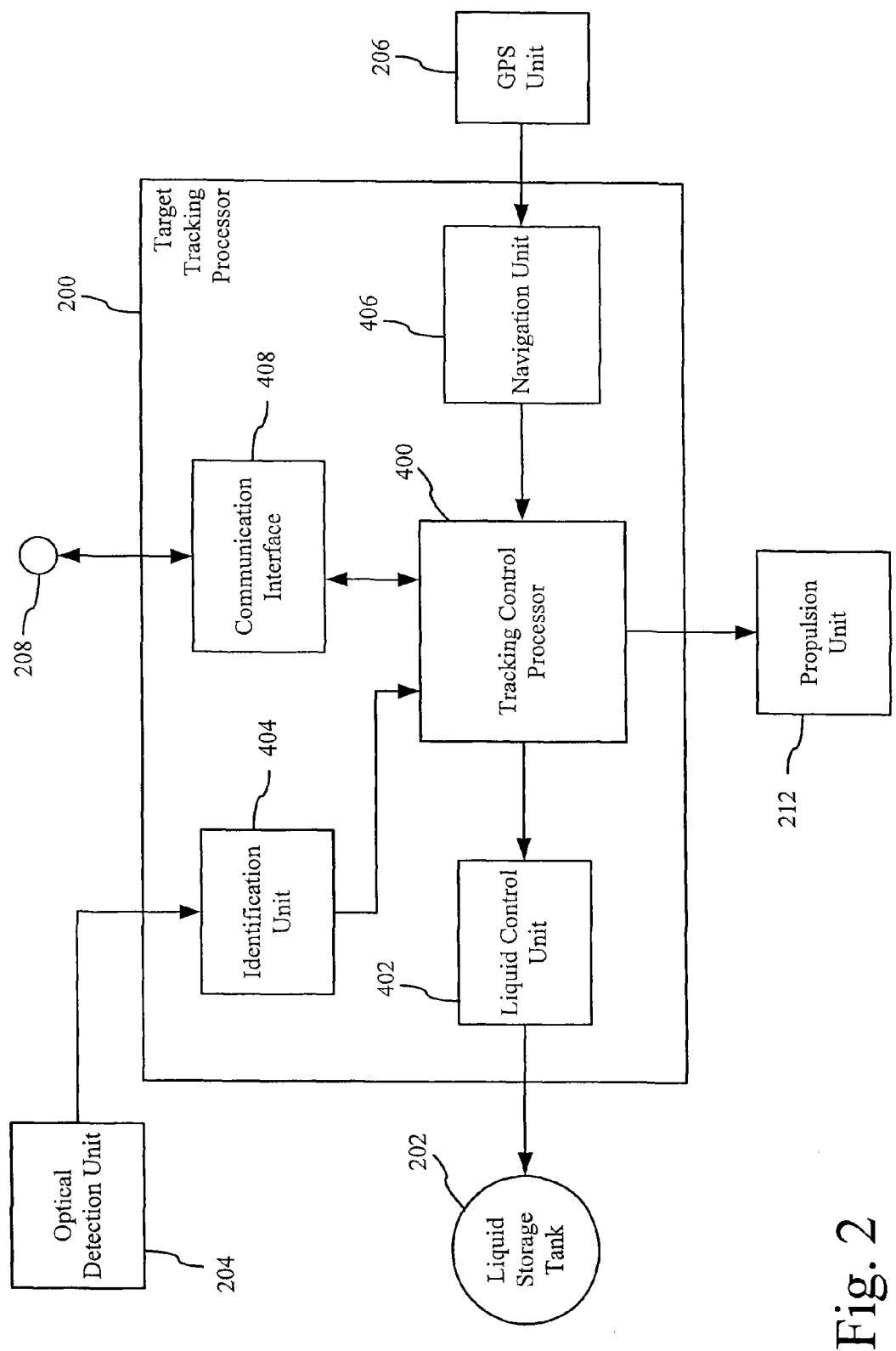
FIG. 2 is a block diagram of a target tracking processor of the mobile tracking and subduing apparatus according to an exemplary embodiment.

The propulsion unit 212 provides the motive force for the mobile tracking and subduing apparatus 20. In the present embodiments, the propulsion unit 212 is the MAV. The propulsion unit 212, however, can be any relevant vehicular platform that provides the motive force for the mobile tracking and subduing apparatus 20. The FIG. 2 is a block diagram of an exemplary target tracking processor 200. The tracking processor 200 receives inputs from the optical detection unit 204, GPS unit 206, and antenna 208. The target tracking processor 200 includes a tracking control processor 400, a liquid control unit 402, an identification unit 404, a navigation unit 406, and a communication interface 408.

The tracking control processor 400 receives processed data from the identification unit 404, the communication interface 408, and the navigation unit 406 and outputs control signals to the liquid control unit 402 based on the received processed data. The tracking control processor may also generate and send signals and messages to the communication interface for transmitting to a remote facility via the antenna 208. The tracking control processor can also generate control signals to an avionic controller (or propulsion unit 212) of the MAV platform based on the received inputs and commands.

The liquid control unit 402 controls the dispensing of the contents of the liquid storage tank 202 via the probe 203 upon receipt of a triggering signal from the tracking control processor 400. The liquid control unit 402 can control the liquid storage tank 202 so as to dispense all or only a portion of the contents of the liquid storage tank 202. The liquid control unit 402 can control the dispensing of the contents of the liquid storage tank 202 through any appropriate mechanism such as a controlling a plunging device, a bellows device, a spring operated device, or any form of mechanism that creates a pressure differential to inject the contents of the liquid storage tank 202 into the target object 10 through the probe 203.

The liquid control unit 402 can also control the liquid storage tank to perform similar functions as those previously discussed to extract a liquid from the target object 10 using the probe 201 and store the extracted liquid in the liquid storage tank 202.

The identification unit 404 receives image and/or video data from the optical detection unit and processes the data to obtain recognition points or identify familiar shapes or features. This may be done by comparing the received image or video data to predetermined features or contents such as an image of the target object 10 stored within the identification unit 404. If the features or content within the received data match, or closely correlate within a predetermined threshold, to the target object 10, then a confirmation signal is generated to the tracking control processor 400 that the target object had been detected.

The navigation unit 406 receives calculated positional data from the GPS unit 206 and generates navigation information such as speed, direction, altitude, and the such. Once the target object has 10 been identified by the identification unit 404, the navigation unit 406 can also generate speed, direction, and other tracking information specific to the target object 10 and send this information to the tracking control processor 400. The tracking control processor 400 can use this information to send appropriate signals to the avionic controller of the MAV platform in order to perform various navigation functions such as traveling from one position to another, prosecuting the target object 10, or approaching the target object 10 in order to inject the contents of the liquid storage tank 202 into the target object.

The communication interface 408 processes the wireless communication signals received from the antenna 208. The processing can be any form of communication processing as applied to any form of communication protocol. Communication protocols that may be supported may be those included in cellular, WiFi, satellite, or similar communication networks. The communication interface 408 would appropriately decode and demodulate the received communication signals and send the extracted data, signals, messages, or instructions to the tracking control processor 400. The communication interface 408 may also encode and modulate communication signals from the tracking control processor 400 to be transmitted to the remote facility via the antenna 208 based on the frequency plan and the communication network being used.

Figure 3:
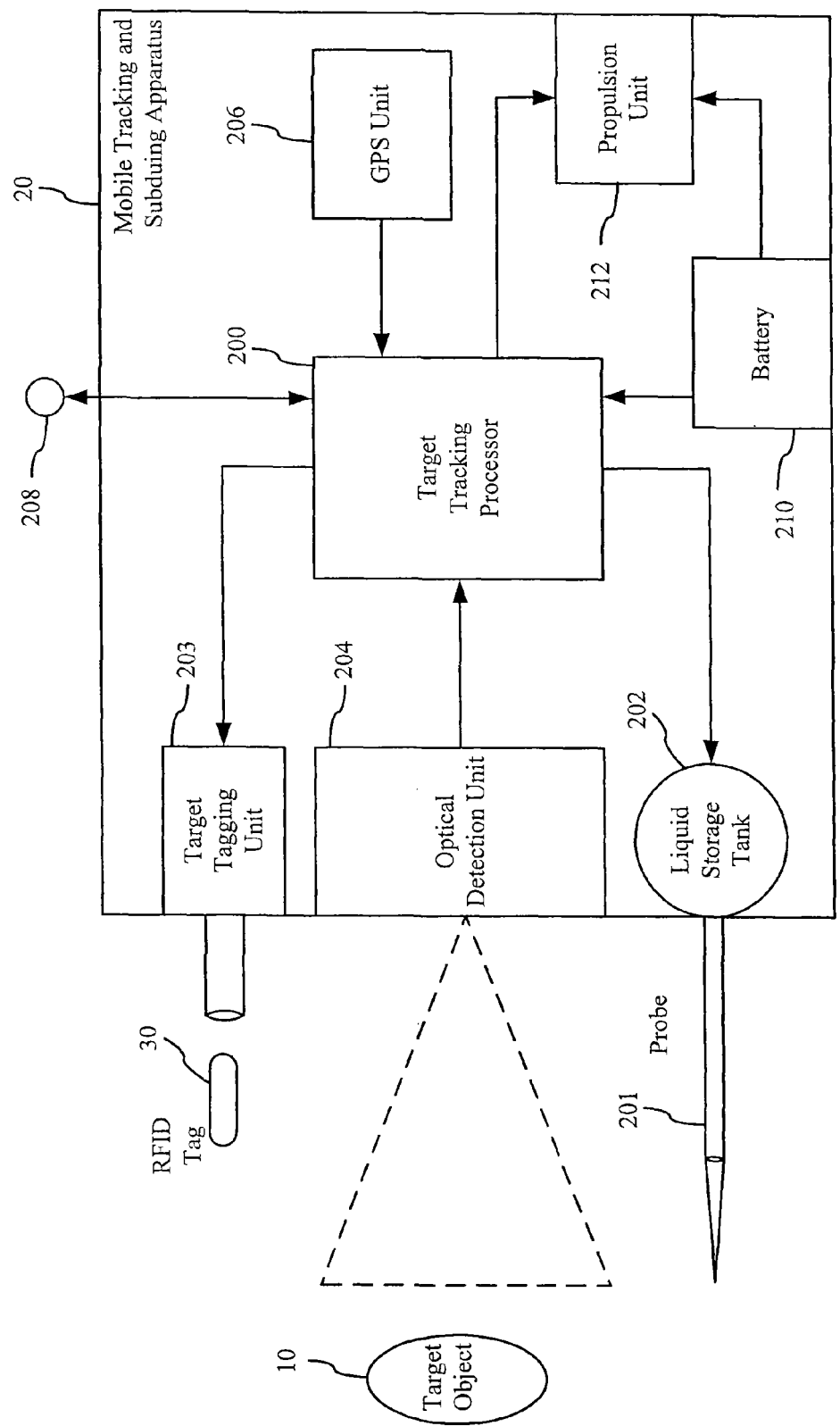
FIG. 3 is a block diagram of a mobile tracking and subduing apparatus further including a target tagging unit according to an exemplary embodiment.

In another embodiment, FIG. 3 is a block diagram of the mobile tracking and subduing apparatus 20 for tracking and subduing a target object further including a target tagging unit 203. The target tagging unit 203 ejects or attaches a RFID tag 30 onto the target object 10 which can be used for enhanced tracking functionality. The RFID tag 30 disposed on to the target object 10 can be either and active RFID tag or passive RFID tag. The RFID tag can be tracked using any appropriate tracking system such as the Mobile Tracking Identification System described in U.S. patent application Ser. No. 13/446, 037, which is herein incorporated by reference in its entirety.

Figure 4:
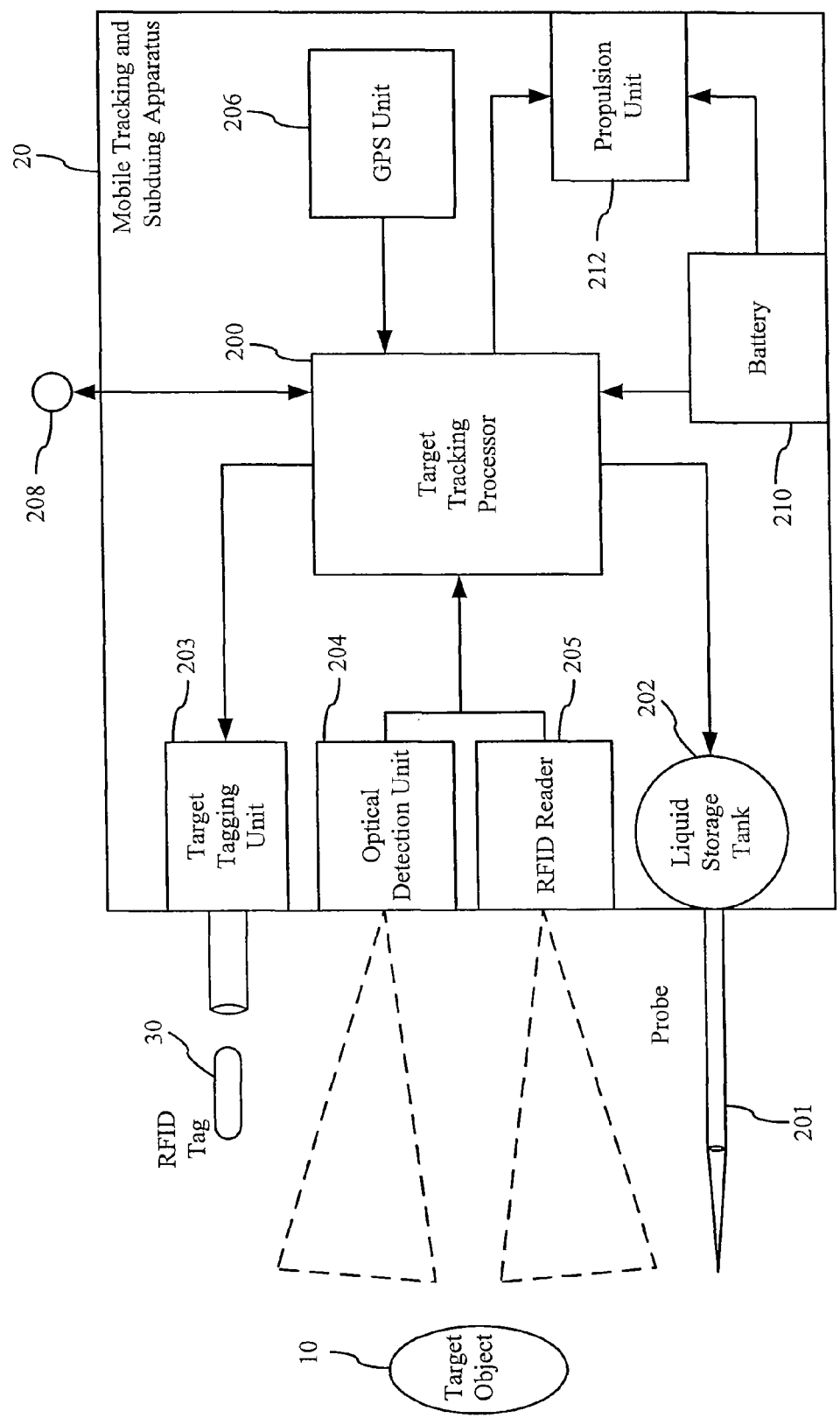
FIG. 4 is a block diagram of a mobile tracking and subduing apparatus further including a RFID reader according to an exemplary embodiment.

In another embodiment, FIG. 4 is a block diagram of the mobile tracking and subduing apparatus 20 for tracking and subduing a target object further including an RFID reader 205. The RFID reader 205 may read active or passive RFID tags and decode the RFID transmission in order to identify a particular RFID tag such as the RFID tag 30 from the target tagging unit 203.

As previously discussed. the mobile tracking and subduing apparatus 20 for tracking and subduing a target object 10 can be integrated into any form of mobile autonomous vehicle to include a micro air vehicle, micro land vehicle, or micro submersible vehicle platforms. In order to maximize the inconspicuous operations of the mobile tracking and subduing apparatus 20, it is preferable that the vehicle platform take a form similar to that of an insect, such as a mosquito or ant, or that of a small mammal or amphibian, such as a dolphin.

Figure 5:
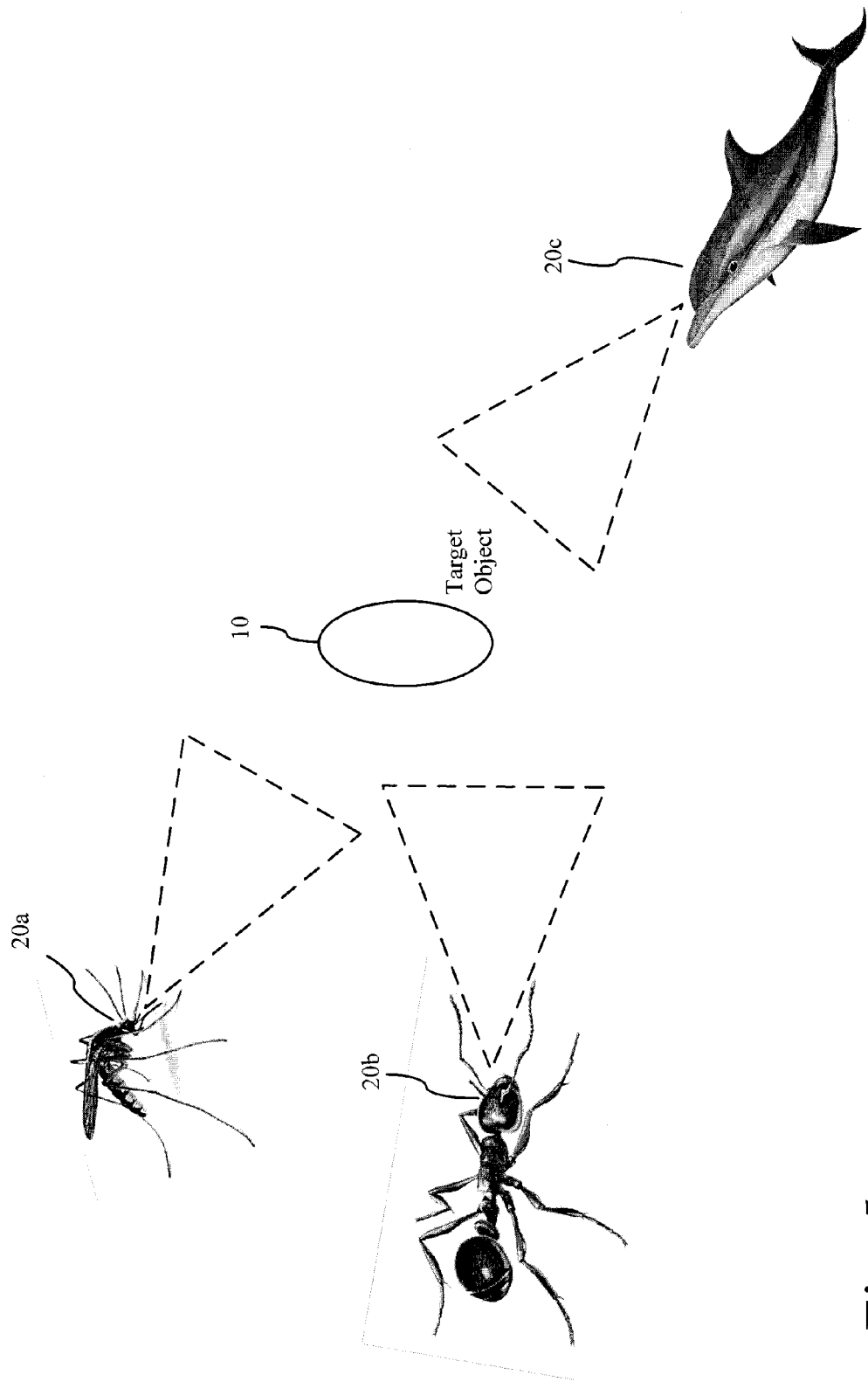
FIG. 5 illustrates various implementations of the mobile tracking and subduing apparatus

In other embodiment, FIG. 5 illustrates various vehicle platforms that that take inconspicuous forms. These inconspicuous forms include examples such as a micro air vehicle that that takes a form similar to that of a mosquito and carries a mobile tracking and subduing apparatus 20*a*, a micro land vehicle that takes a form similar to that of an ant and carries a mobile tracking and subduing apparatus 20*b*, and a micro submersible vehicle that takes a form similar to that of a dolphin and carries a mobile tracking and subduing apparatus 20*c*. By integrating the mobile tracking and subduing apparatus 20 into these more inconspicuous vehicle platforms, more effective detection and tracking of the target object 10 as well as a higher probability of successful subduing and incapacitation of the target object 10 can be achieved. It is important to note that while a mosquito, ant, and dolphin are presented as examples of this embodiment, the mobile tracking and subduing apparatus 20 can be integrated into any size, shape, and form of vehicle platform.

Figure 6:
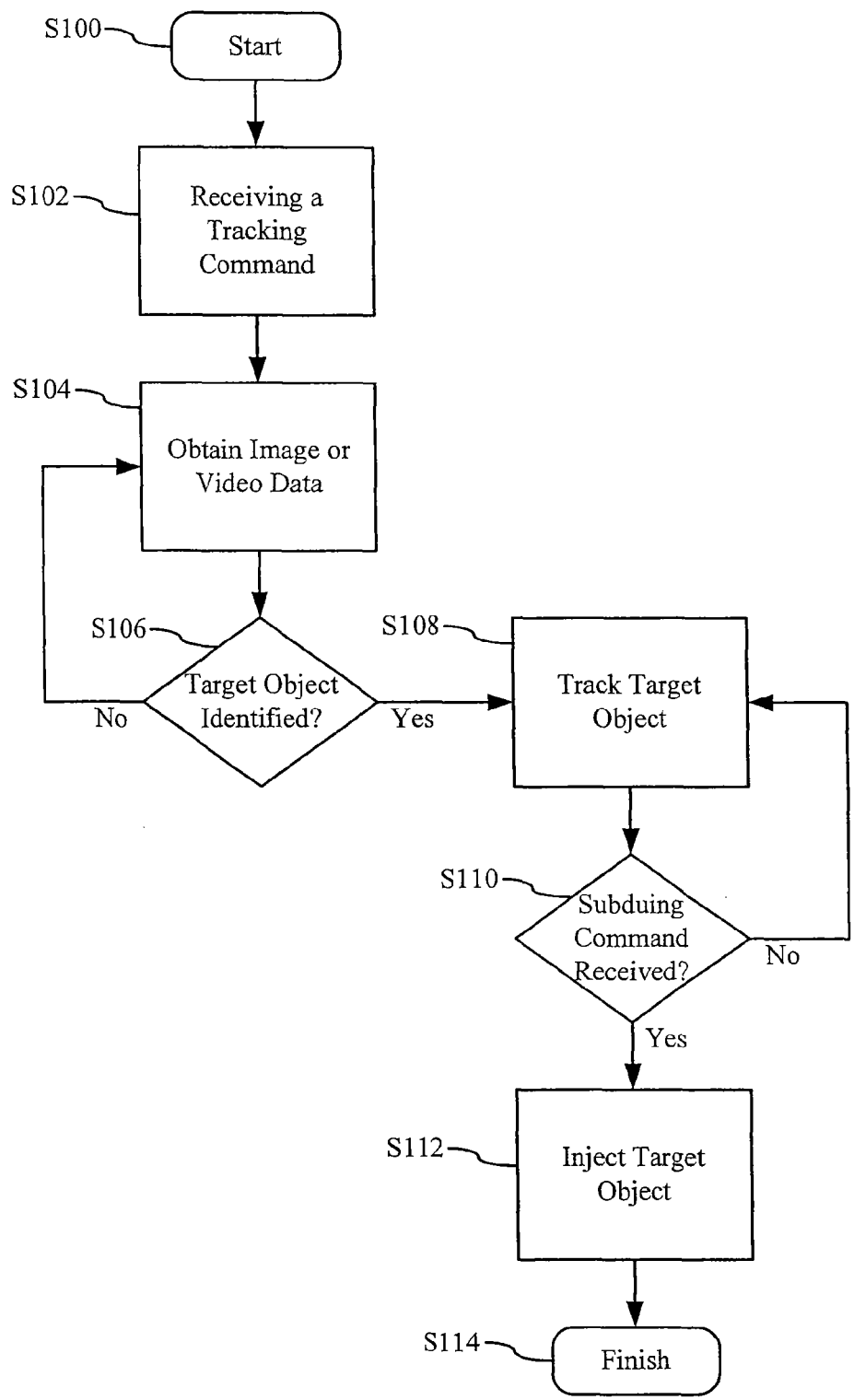
FIG. 6 is a flow chart of a process for detecting, tracking, and subduing a target object according to an exemplary embodiment.

FIG. 6 is a sequence diagram of a mobile tracking and subduing apparatus 20 for tracking and subduing a target object according to an exemplary embodiment. Initially, the mobile tracking and subduing apparatus 20 may be standing by at step S100 to receive tracking command data. When tracking command data is receive at step S102, the mobile tracking and subduing apparatus 20 will process the data and may determine that the target object 10 must be tracked and subdued. The mobile tracking and subduing apparatus 20 will then begin to prosecute the target object 10 by obtaining image or video data of an area where the target object may be located at step S104. When objects and features of the surrounding location are captured by the optical detection unit 204 as image data, the image data is processed by the identification unit 404 to determine if the target object 10 has been located. If the target object has not been identified at step S106, the mobile tracking and subduing apparatus 20 continues to obtain image data at step S104. If the target object 10 has been identified by the identification unit 404 at step S106, the mobile tracking and subduing apparatus 20 commences tracking the target object 10 at step S108.

At this point, a command to subdue or incapacitate the target object 10 may or may not have been received at step S110. If the command to subdue or incapacitate the target object 10 has not been received at step S110, the mobile tracking and subduing apparatus 20 continues prosecution and tracking of the target object 10 at step S108. Once a command to subdue or incapacitate the target object has been received at step S110, the mobile tracking and subduing apparatus 20 approaches the target object 10 to within an appropriate distance needed in insert the probe 201 into the target object 10. The mobile tracking and subduing apparatus 20 then subdues the target object by sending a signal to the liquid control unit 402 to inject the contents of the liquid storage tank 202 into the target object 10 via the probe 201 at step S112. Once the target object has been subdued, the mobile tracking and subduing apparatus 20 will stop prosecuting the target object 10 at step S114.

In addition to injecting the contents of the liquid storage tank 202 into the target object 10, the mobile tracking and subduing apparatus 20 can also extract a liquid from the target object 10 using the probe 201 and store the extracted liquid in the liquid storage tank 202. This would be useful, for example, when a more precise confirmation of the identity or substance of the target object 10 is required or, in the case the target object 10 is a human, DNA is needed for processing or intelligence operations.

Figure 7:
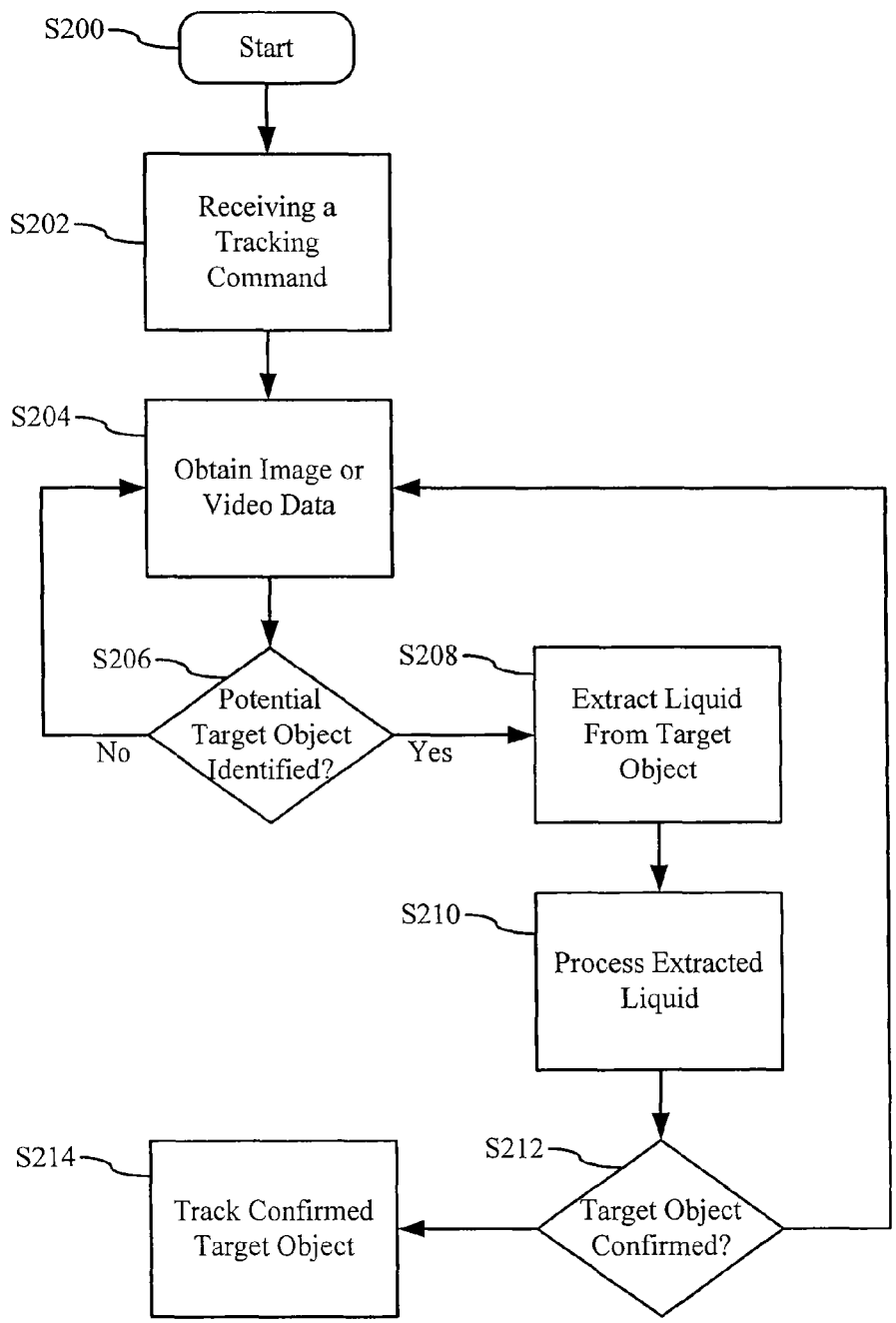
FIG. 7 is a flow chart of a process for detecting, tracking, and extracting a liquid from a target object according to an exemplary embodiment.

FIG. 7 is a sequence diagram of a mobile tracking and subduing apparatus 20 for tracking and extracting a liquid from the target object 10 according to an exemplary embodiment. Initially, the mobile tracking and subduing apparatus 20 may be standing by at step S200 to receive tracking command data. When tracking command data is receive at step S202, the mobile tracking and subduing apparatus 20 will process the data and may determined the target object 10 must be tracked and liquid extracted. The mobile tracking and subduing apparatus 20 will then begin to prosecute the target object 10 by obtaining image or video data of an area where the target object may be located at step S204. When objects and features of the surrounding location are captured by the optical detection unit 204 as image data, the image data is processed by the identification unit 404 to determine if the target object 10 has been located.

At this point, there may still be a question of if the target object 10 identified by the identification unit 404 is actually the desired target object 10 and may be referred to a potential target object. If a potential target object has not been identified at step S206, the mobile tracking and subduing apparatus 20 continues to obtain image data at step S204. If a potential target object has been identified by the identification unit 404 at step S206, the mobile tracking and subduing apparatus 20 attempts to extract a liquid, blood for example, from the potential target object. The mobile tracking and subduing apparatus 20 will then attempt to extract the liquid from the potential target object at step S208. Once the blood from the potential target object has been extracted, the extracted blood will be processed at step S212. The processing of the extracted blood can be performed on board the mobile tracking and subduing apparatus 20 using a simple test such as, for example, a blood type test, or the mobile tracking and subduing apparatus 20 can return to a designated facility where more involved tests, such as DNA tests, can be performed on the extracted blood. Through either of the above methods, the potential target object may or may not be confirmed as the target object 10 at step S212. If the target object 10 has been confirmed by processing the extracted blood at step S212, the mobile tracking and subduing apparatus 20 will commence tracking and prosecuting the target object 10 at step S214. If the target object 10 has not been confirmed as step S212, the mobile tracking and subduing apparatus 20 may return to obtaining image or video data of the surrounding area at step S204 to obtain another potential target object.

In addition to the previously discussed subduing and incapacitation functions of the mobile tracking and subduing apparatus 20, additional features may include those relating to healing and medicinal functions of the mobile tracking and subduing apparatus 20. For example, if an emergency situation arises where the target object 10 has a heart attack or goes into diabetic shock, the mobile tracking and subduing apparatus 20 can use a similar process to the illustrated in FIG. 6 to inject medication such as adrenaline or insulin into the target object 10. In this scenario, an ambulatory care function is provided vice a subduing or incapacitation function.

In another embodiment, the mobile tracking and subduing apparatus 20 can be developed and fabricated using nanotechnology implementations in order to maximize the inconspicuous aspects of the mobile tracking and subduing apparatus 20 and the vehicle platform in which it has been integrated. Certain features and components of the mobile tracking and subduing apparatus 20 may be constructed or implemented using nanotechnology implementations such as memory storage, power generation, or even receiving and transmitting communication signals.

Figure 8:
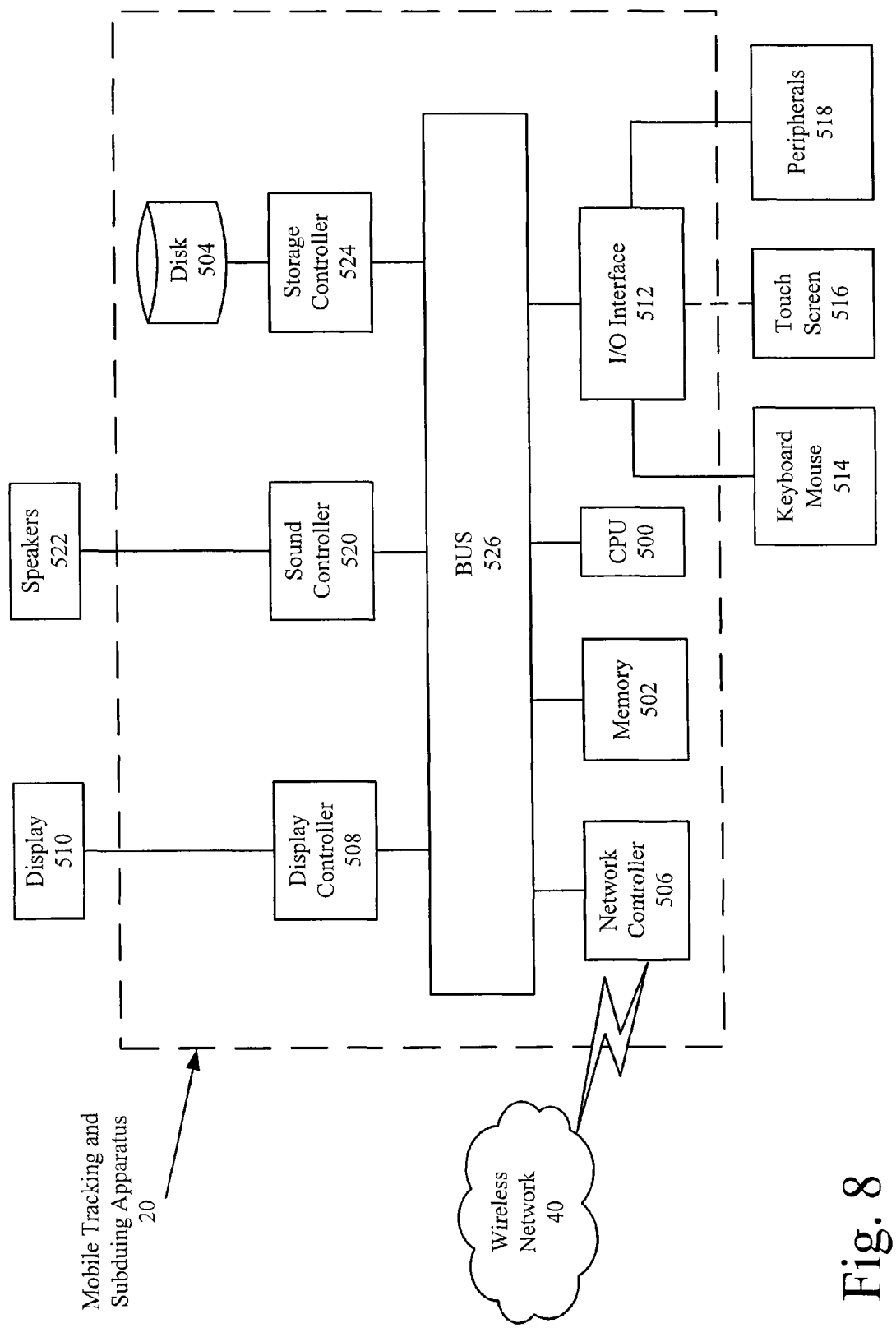
FIG. 8 is a hardware block diagram of a target tracking processor according to an exemplary embodiment.

Next, a hardware description of the mobile tracking and subduing apparatus 20 according to exemplary embodiments is described with reference to FIG. 8. In FIG. 8, the mobile tracking and subduing apparatus 20 includes a CPU 500 which performs the processes described above. The process data and instructions may be stored in memory 502. These processes and instructions may also be stored on a storage medium disk 504 such as a hard drive (HDD) or portable storage medium or may be stored remotely. Further, the claimed advancements are not limited by the form of the computer-readable media on which the instructions of the inventive process are stored. For example, the instructions may be stored on CDs, DVDs, in FLASH memory, RAM, ROM, PROM, EPROM, EEPROM, hard disk or any other information processing device with which the mobile tracking and subduing apparatus 20 communicates, such as a server or computer.

Further, the claimed advancements may be provided as a utility application, background daemon, or component of an operating system, or combination thereof, executing in conjunction with CPU 500 and an operating system such as Microsoft Windows 7, UNIX, Solaris, LINUX, Apple MAC-OS and other systems known to those skilled in the art.

CPU 500 may be a Xenon or Core processor from Intel of America or an Opteron processor from AMD of America, or may be other processor types that would be recognized by one of ordinary skill in the art. Alternatively, the CPU 500 may be implemented on an FPGA, ASIC, PLD or using discrete logic circuits, as one of ordinary skill in the art would recognize. Further, CPU 500 may be implemented as multiple processors cooperatively working in parallel to perform the instructions of the inventive processes described above.

The mobile tracking and subduing apparatus 20 in FIG. 8 also includes a network controller 506, such as an Intel Ethernet PRO network interface card from Intel Corporation of America, for interfacing with network 40. As can be appreciated, the network 40 can be a public network, such as the Internet, or a private network such as an LAN or WAN network, or any combination thereof and can also include PSTN or ISDN sub-networks. The network 40 can also be wired, such as an Ethernet network, or can be wireless such as a cellular network including EDGE, 3G and 4G wireless cellular systems. The wireless network can also be WiFi, Bluetooth, or any other wireless form of communication that is known.

The mobile tracking and subduing apparatus 20 further includes a display controller 508, such as a NVIDIA GeForce GTX or Quadro graphics adaptor from NVIDIA Corporation of America for interfacing with display 510, such as a Hewlett Packard HPL2445w LCD monitor. A general purpose I/O interface 512 interfaces with a keyboard and/or mouse 514 as well as a touch screen panel 516 on or separate from display 510. General purpose I/O interface also connects to a variety of peripherals 518 including printers and scanners, such as an OfficeJet or DeskJet from Hewlett Packard.

A sound controller 520 is also provided in the mobile tracking and subduing apparatus 20, such as Sound Blaster X-Fi Titanium from Creative, to interface with speakers/microphone 522 thereby providing sounds and/or music. The speakers/microphone 522 can also be used to accept dictated words as commands for controlling the mobile tracking and subduing apparatus 20 or for providing location and/or property information with respect to the target property.

The general purpose storage controller 524 connects the storage medium disk 504 with communication bus 526, which may be an ISA, EISA, VESA, PCI, or similar, for interconnecting all of the components of the mobile tracking and subduing apparatus 20. A description of the general features and functionality of the display 510, keyboard and/or mouse 514, as well as the display controller 508, storage controller 524, network controller 506, sound controller 520, and general purpose I/O interface 512 is omitted herein for brevity as these features are known.

What is claimed is:

1. A Micro Arial Vehicle (MAV), including a mobile tracking and subduing apparatus comprising:
    an optical detection unit configured to obtain image data;
    a GPS unit configured to generate positional data of a target object;
    an antenna configured to transmit and receive communication data, the received communication data including a subduing command;
    a liquid storage tank configured to hold a predetermined amount of a liquid;
    a probe configured to be inserted into the target object and to inject the predetermined amount of the liquid from the liquid storage tank into the target object; and
    a target tracking processor configured to
        detect, identify and track the target object by processing the positional data generated by the GPS unit, the communication data received by the antenna and the image data obtained by the optical detection unit, and
        subdue the target object, in response to the subduing command received by the antenna, by controlling the probe to be inserted into the target object, and controlling the probe to inject the predetermined amount of the liquid from the liquid storage section into the target object.

2. The mobile tracking and subduing apparatus of claim 1, wherein the target tracking processor is further configured to
    compare the image data obtained by the optical detection unit to stored data to confirm an identification of the target object,
    control the mobile tracking and subduing apparatus to move in a direction of the target object based on the positional data generated by the GPS unit,
    control the probe to be inserted into the target object, and control the liquid storage tank to the predetermined amount of a liquid to be injected by via the probe into the target object.

3. The mobile tracking and subduing apparatus of claim 1, further comprising:
a target tagging unit configured to attach an RFID tag to the target object, wherein
the target tracking processor is further configured to control the target tagging unit to attach the RFID tag to the target object.

4. The mobile tracking and subduing apparatus of claim 3, further comprising:
an RFID reader configured to read the RFID tag which has been attached to the target object by the target tagging unit, and output RFID data of the target object, wherein
the target tracking processor is further configured to
control the RFID reader to read the RFID tag,
process the RFID data, and
control the antenna to transmit the RFID data.

5. The mobile tracking and subduing apparatus of claim 1, wherein
the probe is further configured to be extend and retract from a protective sheath using a spring mechanism.

6. The mobile tracking and subduing apparatus of claim 1, wherein
the liquid storage tank is further configured to receive and store, via the probe, a target liquid from the target object, and
the target tracking processor is further configured to control the probe to extract the target liquid from the target object, and control the probe to dispense the target liquid to the liquid storage tank.

7. The mobile tracking and subduing apparatus of claim 5, wherein
the liquid storage tank is further configured to store a medicinal liquid for injection into the target object,
the target tracking processor is further configured to process the image data to detect a medical condition of the target object, and control the probe to inject the medicinal liquid into the target object based on the detected medical condition of the target object.

8. The mobile tracking and subduing apparatus of claim 1, wherein
the mobile tracking and subduing apparatus is configured to be integrated onto an aerial platform having a size and appearance of a flying insect.

9. The mobile tracking and subduing apparatus of claim 1, wherein
the mobile tracking and subduing apparatus is configured to be integrated onto a submersible dolphin-sized and shaped platform.

10. The mobile tracking and subduing apparatus of claim 1, wherein
the mobile tracking and subduing apparatus is configured to be integrated onto a land based ant-sized and shaped platform.

11. A Micro Arial Vehicle (MAV), including a mobile tracking and subduing method comprising:
receiving, via an antenna, communication data including a subduing command;
generating, via a GPS unit, positional data of a target object;
obtaining, via an optical detection unit, image data of the target object;
detecting, by a target tracking processor, a plurality of features of the target object;
identifying, by the target tracking processor, the target object by comparing the plurality of detected features of the target object to stored data;
tracking, by the target tracking processor, the target object based on the received communication data and the generated positional data; and
subduing the target object, in response to the subduing command received by the antenna, by controlling a probe to be inserted into the target object, and controlling the probe to inject a predetermined amount of a liquid into the identified target object.

12. The mobile tracking and subduing method of claim 11, further comprising:
moving in a direction of the target object based on the positional data generated by the GPS unit.

13. The mobile tracking and subduing method of claim 11, further comprising:
attaching an RFID tag to the target object.

14. The mobile tracking and subduing method of claim 13, further comprising:
reading the RFID tag attached to the target object;
processing, by the target tracking processor, RFID data based on the read RFID tag; and
transmitting, by the antenna, the RFID data.

15. The mobile tracking and subduing method of claim 11, further comprising:
extending the probe from a protective sheath; and
retracting the probe into the protective sheath.

16. The mobile tracking and subduing method of claim 11, further comprising:
processing, by the target tracking processor, the image data to detect a medical condition of the target object; and
injecting a medicinal liquid into the target object.

17. The mobile tracking and subduing method of claim 11, further comprising:
controlling the probe to extract a target liquid from the target object.

18. A Micro Arial Vehicle (MAV), including a non-transitory computer-readable storage medium with computer readable instructions stored therein that when executed by a computer, cause the computer to execute a method comprising:
receiving, via an antenna, communication data including a subduing command;
generating, via a GPS unit, positional data of a target object;
obtaining, via an optical detection unit, image data of the target object;
detecting, by a target tracking processor, a plurality of features of the target object;
identifying, by the target tracking processor, the target object by comparing the plurality of detected features of the target object to stored data;
tracking, by the target tracking processor, the target object based on the received communication data and the generated positional data; and
subduing the target object, in response to the subduing command received by the antenna, by controlling a probe to be inserted into the target object, and controlling the probe to inject a predetermined amount of a liquid into the identified target object.

* * * * *